(12) United States Patent
Kataoka et al.

(10) Patent No.: US 11,703,441 B2
(45) Date of Patent: Jul. 18, 2023

(54) METHOD FOR PREDICTING ONSET OF CEREBRAL INFARCTION, METHOD FOR DETERMINING THERAPEUTIC EFFECT OF ERYTHROPOIETIC FACTOR PREPARATION, AND METHOD FOR DETERMINING STAGE OF CHRONIC KIDNEY

(71) Applicants: KAWASAKI GAKUEN Educational Foundation, Kurashiki (JP); THE UNIVERSITY OF TOKYO, Tokyo (JP); SYSMEX CORPORATION, Kobe (JP)

(72) Inventors: Hiromi Kataoka, Kurashiki (JP); Yutaka Yatomi, Tokyo (JP); Akiko Masuda, Tokyo (JP); Hironori Shimosaka, Toyko (JP); Hajimu Kawakami, Kobe (JP)

(73) Assignees: KAWASAKI GAKUEN Educational Foundation, Kurashiki (JP); THE UNIVERSITY OF TOKYO, Tokyo (JP); SYSMEX CORPORATION, Kobe (JP)

( * ) Notice: Subject to any disclaimer, the term of this patent is extended or adjusted under 35 U.S.C. 154(b) by 1280 days.

(21) Appl. No.: 16/145,824

(22) Filed: Sep. 28, 2018

(65) Prior Publication Data

US 2019/0101483 A1 Apr. 4, 2019

(30) Foreign Application Priority Data

Sep. 29, 2017 (JP) ................................. 2017-190676

(51) Int. Cl.
*G01N 15/10* (2006.01)
*G01N 15/14* (2006.01)
(Continued)

(52) U.S. Cl.
CPC ......... *G01N 15/1031* (2013.01); *G01N 15/14* (2013.01); *G16H 50/20* (2018.01);
(Continued)

(58) Field of Classification Search
CPC ... G01N 2015/1006; G01N 2015/1062; G01N 2015/0073; G01N 2015/1486;
(Continued)

(56) References Cited

U.S. PATENT DOCUMENTS

| 2005/0255001 | A1* | 11/2005 | Padmanabhan | .... G01N 15/1404 |
| | | | | 436/63 |
| 2010/0248300 | A1* | 9/2010 | Yoshida | ............. G01N 15/1459 |
| | | | | 435/39 |
| 2015/0276720 | A1 | 10/2015 | Abe et al. | |

OTHER PUBLICATIONS

Office Action, dated Aug. 24, 2021, issued by the Japanese Patent Office in corresponding Japanese English Patent Application No. 2017-190676.

(Continued)

*Primary Examiner* — Sang H Nguyen
(74) *Attorney, Agent, or Firm* — Sughrue Mion, PLLC

(57) ABSTRACT

Disclosed is a method for assisting prediction of onset of cerebral infarction, based on the number of red blood cells contained in a blood sample collected from a subject, comprising the steps of:
calculating an exponent value for the prediction from a first measured value indicating red blood cell count measured by electrical resistance measurement method and a second measured value indicating red blood cell count measured by optical measurement method,
comparing the exponent value with a reference range, and suggesting that the subject develops cerebral infarction when the exponent value is outside the reference range.

7 Claims, 14 Drawing Sheets

(51) Int. Cl.
  *G01N 33/49*  (2006.01)
  *G16H 50/20*  (2018.01)
  *G16H 50/30*  (2018.01)
  *G01N 15/00*  (2006.01)

(52) U.S. Cl.
  CPC ......... *G16H 50/30* (2018.01); *G01N 15/1459* (2013.01); *G01N 33/49* (2013.01); *G01N 2015/0073* (2013.01); *G01N 2015/1006* (2013.01); *G01N 2015/1062* (2013.01); *G01N 2015/1486* (2013.01)

(58) Field of Classification Search
  CPC ............... G01N 15/1459; G01N 15/14; G01N 15/1031; G01N 33/49; G16H 50/20; G16H 50/30
  See application file for complete search history.

(56) References Cited

OTHER PUBLICATIONS

Eloísa Urrechaga et al., "Potential utility of the new Sysmex XE 5000 red blood cell extended parameters in the study of disorders of iron metabolism", Clin Chem Lab Med, 2009, pp. 1411-1416, vol. 47, No. 11.

* cited by examiner

FIG. 9

| REFERENCE RANGE | OUTSIDE REFERENCE RANGE | |
|---|---|---|
| $(I/O) \geq 1$ | $0 < (I/O) < 1$ | $(I/O) : (RBC-I)/(RBC-O)$ |
| $(I-O) \geq 0$ | $(I-O) < 0$ | $(I-O) : [(RBC-I)/(RBC-O)]$ |
| $0 < (O/I) \leq 1$ | $(O/I) > 1$ | $(O/I) : (RBC-O)/(RBC-I)$ |
| $(O-I) \leq 0$ | $(O-I) > 0$ | $(O-I) : [(RBC-O)/(RBC-I)]$ |

METHOD FOR PREDICTING ONSET OF CEREBRAL INFARCTION, METHOD FOR DETERMINING THERAPEUTIC EFFECT OF ERYTHROPOIETIC FACTOR PREPARATION, AND METHOD FOR DETERMINING STAGE OF CHRONIC KIDNEY

CROSS REFERENCE TO RELATED APPLICATIONS

This application claims priority from prior Japanese Patent Application No. 2017-190676, filed on Sep. 29, 2017, entitled "Method for predicting onset of cerebral infarction, method for determining therapeutic effect of erythropoietic factor preparation, and method for determining stage of chronic kidney disease", the entire contents of which are incorporated herein by reference.

TECHNICAL FIELD

The present invention relates to a method for determining the stage of chronic kidney disease based on red blood cell count, a method for determining the therapeutic effect of an erythropoietic factor preparation, and a method for predicting the onset of cerebral infarction.

BACKGROUND

US 2015/276,720 A describes a blood analyzer including a detection unit that performs measurement by a sheath flow DC detection method and a flow cell and optical detector for performing measurement by a flow cytometry method.

In Clin Chem Lab Med 2009; 47(11): 1411-1416, it is shown that red blood cell count of healthy persons and patients with chronic kidney disease (CKD) measured by an automated hemocytometer is decreased as compared to red blood cell count of healthy persons.

SUMMARY

The scope of the present invention is defined solely by the appended claims, and is not affected to any degree by the statements within this summary.

In patients with chronic kidney disease, it is known that the hemoglobin level decreases with stage progression. Red blood cell count is highly correlated with hemoglobin level and shows behavior similar to the hemoglobin level when measured with a general automatic hemocyte counter. Therefore, red blood cell count was not an independent index related to stage determination of chronic kidney disease and renal anemia.

A first embodiment of the present invention relates to a method for assisting prediction of onset of cerebral infarction, based on the number of red blood cells contained in a blood sample collected from a subject. The method comprises the steps of calculating an exponent value for the prediction from a first measured value indicating red blood cell count measured by electrical resistance measurement method and a second measured value indicating red blood cell count measured by optical measurement method, comparing the exponent value with a reference range, and suggesting that the subject develops cerebral infarction when the exponent value is outside the reference range.

A second embodiment of the present invention relates to a method for assisting determination of a therapeutic effect by an erythropoietic factor preparation. The method comprises the steps of, for a blood sample collected from a subject at a first time point, calculating a first exponent value from a first measured value indicating red blood cell count measured by electrical resistance measurement method and a second measured value indicating red blood cell count measured by optical measurement method, for a blood sample collected from the subject at a second time point after administration of the erythropoietic factor preparation and after the first time point, calculating a second exponent value from a third measured value indicating red blood cell count measured by electrical resistance measurement method and a fourth measured value indicating red blood cell count measured by optical measurement method, comparing the first exponent value with the second exponent value, and suggesting that the erythropoietic factor preparation works well in the subject when the second exponent value is determined to be improved over the first exponent value.

A third embodiment of the present invention relates to a method for assisting stage determination of chronic kidney disease, based on the number of red blood cells contained in a blood sample collected from a subject. The method comprises the steps of calculating an exponent value for the determination from a first measured value indicating red blood cell count measured by electrical resistance measurement method and a second measured value indicating red blood cell count measured by optical measurement method, comparing the exponent value with each reference range determined for each stage of chronic kidney disease and determining the reference range containing the exponent value, and suggesting that the subject is a stage corresponding to the reference range determined in the determination step.

A fourth embodiment of the present invention relates to a method for assisting prediction of onset of cerebral infarction, based on the number of red blood cells contained in a blood sample collected from a subject. The method comprises the steps of calculating an exponent value for the prediction from a first measured value indicating red blood cell count in a blood sample not treated with a surfactant and a second measured value indicating red blood cell count in a blood sample treated with a surfactant, comparing the exponent value with a reference range, and suggesting that the subject develops cerebral infarction when the exponent value is outside the reference range.

A fifth embodiment of the present invention relates to a method for assisting determination of a therapeutic effect by an erythropoietic factor preparation. The method comprises the steps of, for a blood sample collected from a subject at a first time point, calculating a first exponent value from a first measured value indicating red blood cell count in a blood sample not treated with a surfactant and a second measured value indicating red blood cell count in a blood sample treated with a surfactant, for a blood sample collected from the subject at a second time point after administration of the erythropoietic factor preparation and after the first time point, calculating a second exponent value from a third measured value indicating red blood cell count in a blood sample not treated with a surfactant and a fourth measured value indicating red blood cell count in a blood sample treated with a surfactant, comparing the first exponent value with the second exponent value, and suggesting that the erythropoietic factor preparation works well in the subject when the second exponent value is determined to be improved over the first exponent value.

A sixth embodiment of the present invention relates to a method for assisting stage determination of chronic kidney disease, based on the number of red blood cells contained in a blood sample collected from a subject. The method comprises the steps of calculating an exponent value for the determination from a first measured value indicating red blood cell count in a blood sample not treated with a surfactant and a second measured value indicating red blood cell count in a blood sample treated with a surfactant, comparing the exponent value with each reference range determined for each stage of chronic kidney disease and determining the reference range containing the exponent value, and suggesting that the subject is a stage corresponding to the reference range determined in the determination step.

BRIEF DESCRIPTION OF THE DRAWINGS

FIG. 9 is a diagram showing a reference range of an exponent value for predicting the onset of cerebral infarction.

DETAILED DESCRIPTION OF THE PREFERRED EMBODIMENTS

[1. Method for Measuring Red Blood Cells]

In each embodiment, red blood cell count measured by the method for measuring red blood cell count of the two measurement principles is used. One measurement method is an electrical resistance measurement method for detecting a change in electrical resistance by cells to measure the number and volume of the cells. The electrical resistance measurement is carried out using a sheath flow DC detector or the like. Another measurement method is an optical measurement method for irradiating cells passing through a flow cell with light and measuring the number and size of the cells by a flow cytometer that detects information of light (side fluorescence, forward scattered light, side scattered light, etc.) emitted from the cells. In the present specification, red blood cell count measured by electrical resistance measurement method is sometimes referred to as "RBC-I", and red blood cell count measured by optical measurement method is sometimes referred to as "RBC-O". The measured value indicating red blood cell count may be indicated by red blood cell count per unit volume or may be the number of peaks of the amplitude of the electric pulse per unit time or the like.

In the electric resistance method, red blood cell count is measured without treating a blood sample containing blood cells with a surfactant before measurement. In the optical measurement method, a blood sample containing blood cells is treated with a surfactant before measurement, and red blood cell count is measured. Therefore, in the present specification, measurement by the electrical resistance measurement method may be replaced with measurement without treating a blood sample with a surfactant before measurement. Measurement by the optical measurement method may be replaced with measurement after treating a blood sample with a surfactant before measurement.

[1-1. Blood Analyzer]

Figure 1:
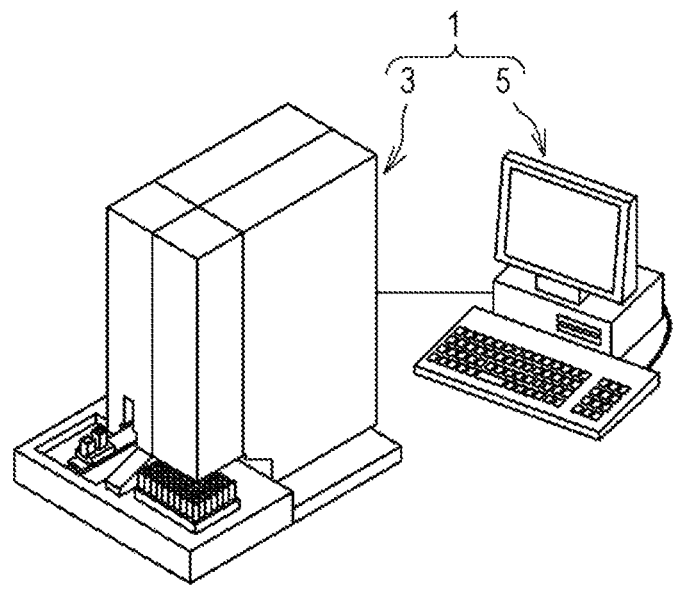
FIG. 1 is an overall view of a blood analyzer.

The method for measuring red blood cell count by electrical resistance measurement method and the method for measuring red blood cell count by optical measurement method are well known, and for example, both can be measured using the blood analyzer shown in FIG. 1.

FIG. 1 shows a blood analyzer (multi-item blood cell counter) 1. The blood analyzer 1 counts blood cells (white blood cells, red blood cells, platelets) contained in a blood sample and analyzes the blood. The blood analyzer 1 includes a measurement unit 3 and an information processing unit 5 that can control the measurement unit 3.

[1-2. Measurement Unit]

Figure 2:
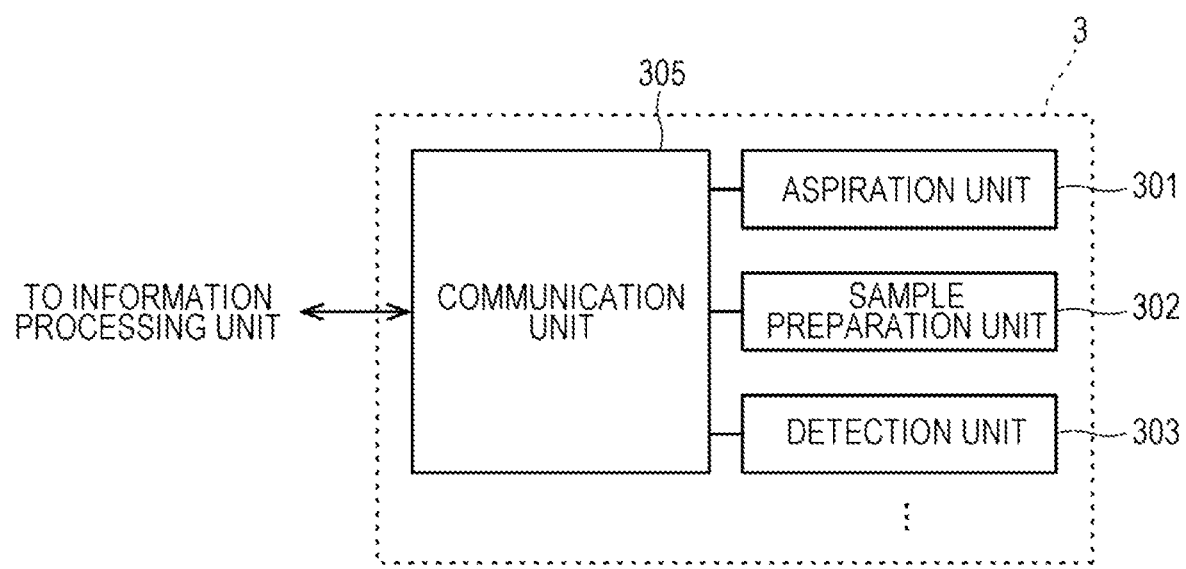
FIG. 2 is a block diagram of a measurement unit.
Figure 3:
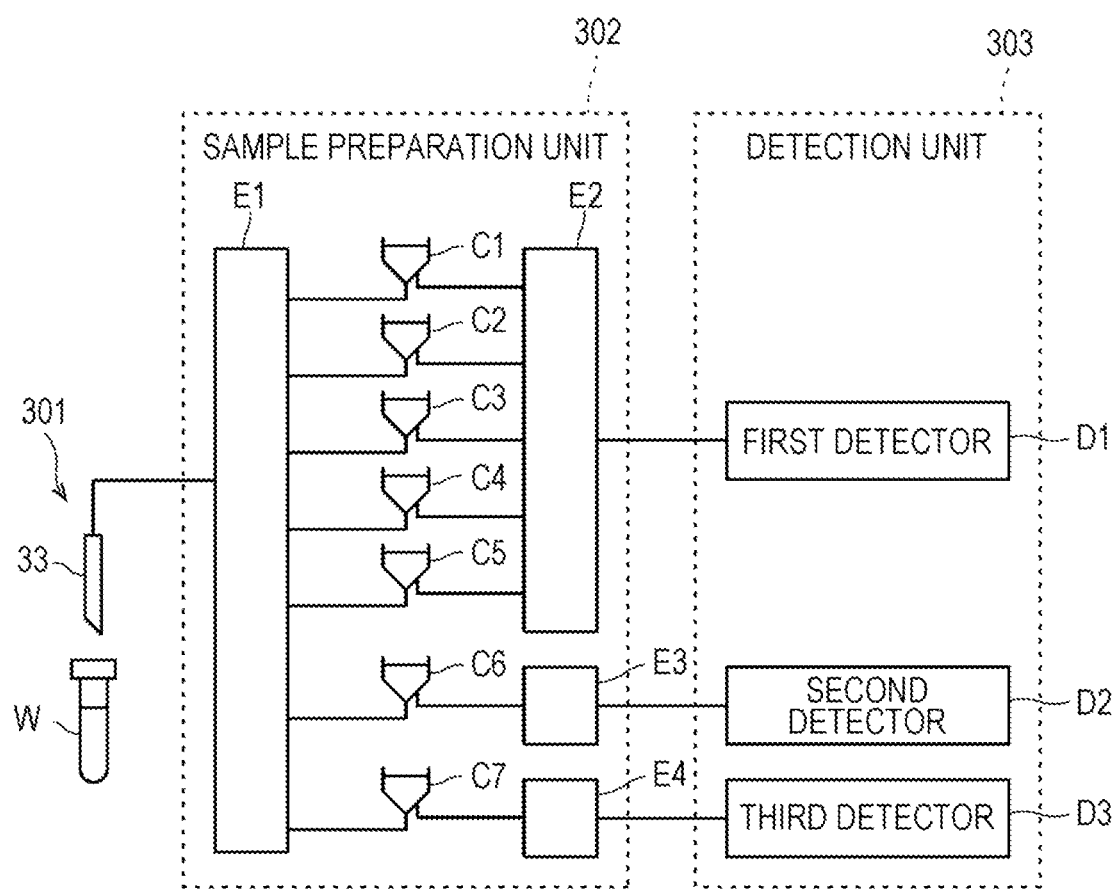
FIG. 3 is a diagram showing a fluid circuit of a measurement unit.

FIGS. 2 and 3 show the configuration of the measurement unit 3. The measurement unit 3 includes an aspiration unit 301, a sample preparation unit 302, a detection unit 303, a communication unit 305, and the like. The aspiration unit 301 aspirates a blood sample from blood sample stored in sample container W. The aspiration unit 301 includes a piercer 33 for aspirating the blood sample in the sample container W.

The sample preparation unit 302 prepares a measurement sample to be used for measurement from the blood sample aspirated by the aspiration unit 301. The detection unit 303 detects blood cells from the measurement sample prepared by the sample preparation unit 302.

In the communication unit 305, the measurement unit 3 communicates with the information processing unit 5. The communication unit 305 receives a control command from the information processing unit 5. The communication unit 305 transmits the measurement data obtained by detection by the detection unit 303 to the information processing unit 5.

The aspiration unit 301, the sample preparation unit 302 and the detection unit 303 each comprise a fluid circuit. This fluid circuit operates to prepare a measurement sample from the blood aspirated by the piercer 33 and give the measurement sample to the detection unit 303. The sample preparation unit 302 includes a first reaction chamber C1 to a seventh reaction chamber C7 for preparing a sample. The detection unit 303 includes a first detector D1 to a third detector D3 that detect the measurement sample.

The fluid circuit constituting the sample preparation unit 302 includes a first fluid circuit E1 to a fourth fluid circuit E4. The fluid circuits E1 to E4 include valves and pumps (not shown) and the like, so that a flow path is switched by the valve, and a fluid such as a blood sample can be transported into the fluid circuit by the pump. The first fluid circuit E1 dispenses a blood sample from the piercer 33 into each of reaction chambers C1 to C7. The first fluid circuit E1 supplies a diluent, a hemolytic agent, a stain solution and the like to each of the reaction chambers C1 to C7 as necessary. Liquids (sample preparation liquids) such as a diluent, a hemolytic agent, a staining solution and the like are used for preparing a measurement sample.

The second fluid circuit E2 transports the measurement sample prepared in the first reaction chamber C1 to the fifth reaction chamber C5 to the first detection unit D1. The third fluid circuit E3 transports the measurement sample prepared in the sixth reaction chamber C6 to the second detection unit D2. The fourth fluid circuit E4 transports the measurement sample prepared in the seventh reaction chamber C7 to the third detection unit D3. When the detection is completed, the measurement samples in the detection units D to D3 are discharged to a waste liquid chamber (not shown).

The first reaction chamber C1 is a reaction chamber for preparing a sample (first sample) for performing analysis on white blood cells/nucleated erythrocytes.

The second reaction chamber C2 is a reaction chamber for preparing a sample (second sample) for performing analysis on leukocyte classification.

The third reaction chamber C3 is a reaction chamber for preparing a sample (third sample) for performing analysis on the number of abnormal cells/immature cells.

The fourth reaction chamber C4 is a reaction chamber for preparing a sample (fourth sample) for performing analysis on erythrocytes and reticulocytes.

The fifth reaction chamber C5 is a reaction chamber for preparing a sample (fifth sample) for performing analysis on platelets.

The sixth reaction chamber C6 is a reaction chamber for preparing a sample (sixth sample) for performing analysis on erythrocytes and platelets.

The seventh reaction chamber C7 is a reaction chamber for preparing a sample (seventh sample) for performing analysis on hemoglobin.

The first detection unit D has a flow cell and an optical detector for performing measurement by a flow cytometry method using a semiconductor laser. Optical information (side fluorescence signal, forward scattered light signal, side scattered light signal) is detected as measurement data from blood cells (white blood cells, red blood cells, platelets, etc.) in the sample by the optical detector.

The first detection unit D1 performs measurement on the first sample (first measurement: measurement for analysis on white blood cells/nucleated erythrocytes), measurement on the second sample (second measurement: measurement for analysis on leukocyte classification), measurement on the third sample (third measurement: measurement for analysis on the number of abnormal cells/immature cells), measurement on the fourth sample (fourth measurement: optical measurement for analysis on erythrocytes and reticulocytes), and measurement on the fifth sample (fifth measurement: measurement for analysis on platelets).

The second detection unit D2 performs measurement by a sheath flow DC detection method. The second detection unit D2 performs measurement on the sixth sample (sixth measurement: electrical resistance measurement for analysis on erythrocytes and platelets).

The third detection unit D3 performs measurement by a SLS-hemoglobin method. The third detection unit D3 performs measurement on the seventh sample (seventh measurement: measurement for analysis on hemoglobin).

The fourth sample is prepared by mixing a blood sample with a reagent containing a surfactant (for example, fluorocell RET manufactured by Sysmex Corporation) before measurement. The blood sample mixed with the reagent may be warmed or mechanical stimulation such as rotation may be applied.

The sixth sample is prepared by mixing a blood sample with a reagent not containing a surfactant (for example, Cell Pack DCL manufactured by Sysmex Corporation) before measurement.

[1-3. Information Processing Unit]

Figure 4:
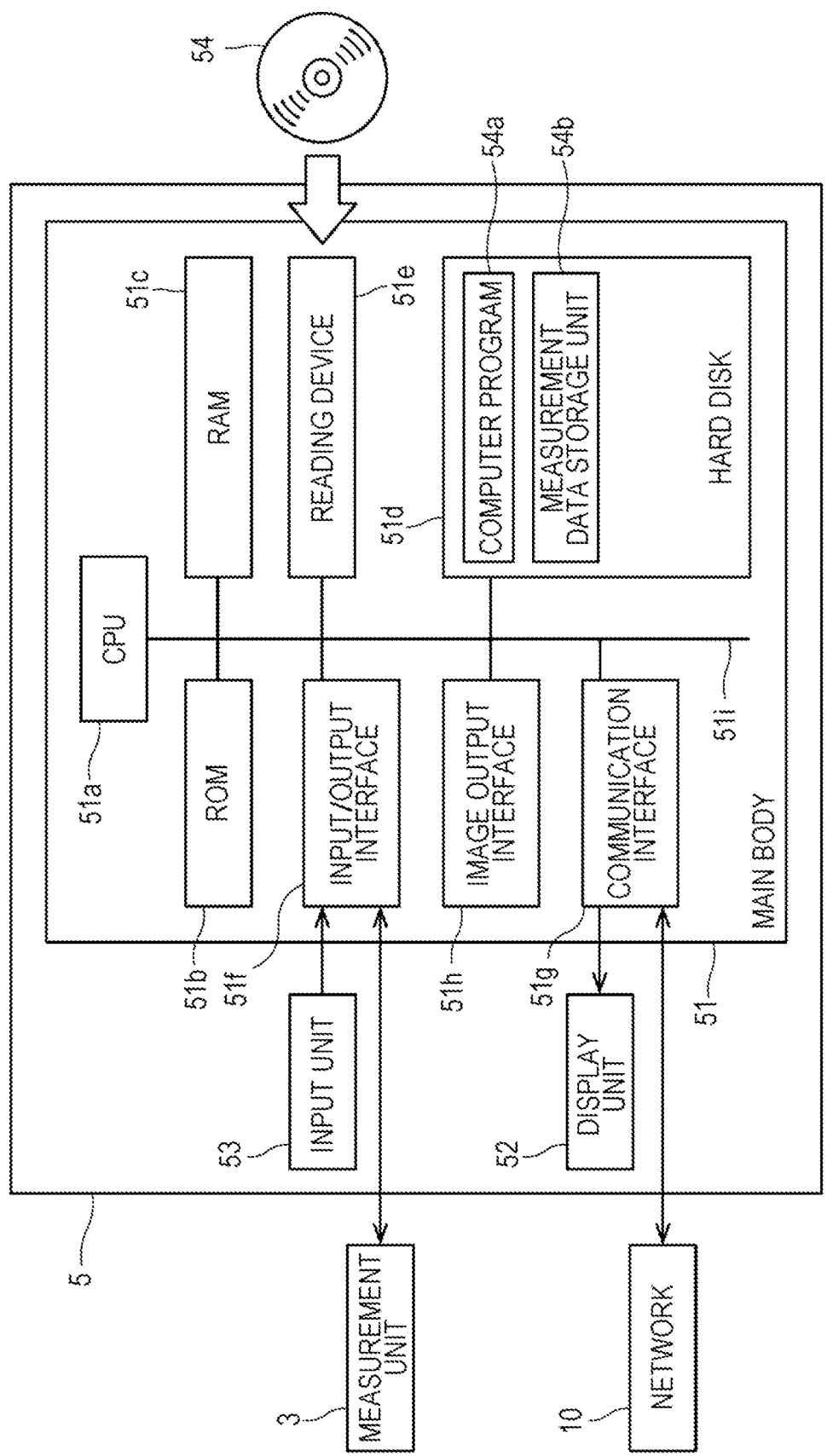
FIG. 4 is a configuration diagram of an information processing unit.

The information processing unit 5 is configured by a computer. FIG. 4 is a block diagram showing a configuration of the information processing unit 5. As shown in FIG. 4, a computer 5 includes a main body (control unit) 51, a display unit (output unit) 52, and an input unit 53. The main body 51 includes a CPU 51a, a ROM 51b, a RAM 51c, a hard disk 51d, a reading device 51e, an input/output interface 51f, a communication interface 51g and an image output interface 51h, and the CPU 51a, the ROM 51b, the RAM 51c, the hard disk 51d, the reading device 51e, the input/output interface 51f, the communication interface 51g and the image output interface 51h are connected via a bus 51i.

The CPU 51a can execute a computer program.

In the hard disk (storage device) 51d, various computer programs 54a to be executed by the CPU 51a, such as operating systems and application programs, and data used for executing the computer programs are installed.

The computer program 54a includes programs for controlling the measurement unit, analyzing the measurement data, outputting information, and the like. The computer program 54a can be recorded on a portable recording medium 54 such as a CD-ROM. The reading device 51e can read the computer program 54a recorded on the recording medium 54.

The computer program 54a is not only provided by the portable recording medium 54 but can also be provided from an external device communicably connected to the computer 5 by a network (whether wired or wireless) through the network.

The hard disk 51d also functions as a measurement data storage unit 54b that stores various data.

The measurement data storage unit 54b stores the measurement data received from the measurement unit 3.

The input/output interface 51f is connected to the measurement unit 3. As a result, the information processing unit 5 can control the measurement unit 3, and the information processing unit 5 can receive measurement data from the measurement unit 3.

The image output interface 51h is connected to a display unit (output unit) 52 configured by a display or the like. Therefore, the information processing unit 5 can display (output) various kinds of information.

[2. Method and Apparatus for Determining Stage of Chronic Kidney Disease]

[1-2. Measurement Method]

One embodiment relates to a method for determining the stage of chronic kidney disease. Determining the stage of chronic kidney disease includes assisting determination of the stage of chronic kidney disease. The method determines the stage of chronic kidney disease based on red blood cell count in a blood sample collected from a subject.

According to "CKD Diagnostic Guide 2012 (edited by Japanese Society of Nephrology)", the stage of chronic kidney disease is divided into six stages of G1, G2, G3a, G3b, G4, and G5 from mild to severe, based on the eGFR division.

In the present embodiment, the subject is not limited, but is preferably a human. The subject may be an individual diagnosed or an individual not diagnosed as having kidney disease. The sex and age of the subject are not limited. It is preferable that the subject to be measured according to the present embodiment is not administered with an erythropoietic factor preparation or 120 days or more has elapsed from the most recent administration of the erythropoietic factor preparation.

In the present embodiment, the blood sample is not limited as long as red blood cell count can be measured. The blood sample is preferably peripheral blood collected using an anticoagulant. Examples of the anticoagulant include sodium heparin, sodium ethylenediaminetetraacetate, potassium ethylenediaminetetraacetate, and the like. The time from collection of the blood sample to measurement is within 24 hours, preferably within 16 hours, more preferably within 12 hours, and further preferably within 8 hours.

In the present embodiment, an exponent value for the determination is initially calculated from a first measured value indicating red blood cell count measured by electrical resistance measurement method and a second measured value indicating red blood cell count measured by optical measurement method. Prior to the calculation of exponent value, for the blood sample collected from a subject, a first measured value indicating red blood cell count measured by the electrical resistance measurement method (RBC-I) and a second measured value indicating red blood cell count measured by the optical measurement method (RBC-O) may be acquired. As the two measured values, the measured values measured by the measurement unit 3 may be acquired directly from the measurement unit 3 or may be acquired via a network (whether wired or wireless). The acquisition includes measuring. The acquisition may be performed by a human or may be performed by a control unit of an apparatus to be described later.

From the first measured value and the second measured value, an exponent value for determining the stage of chronic kidney disease is calculated from the two measured values. The exponent value includes a value obtained by dividing the first measured value by the second measured value ("RBC-I"/"RBC-O"), a value obtained by subtracting the second measured value from the first measured value ("RBC-I"-"RBC-O"), a value obtained by dividing the second measured value by the first measured value ("RBC-O"/"RBC-I"), or a value obtained by subtracting the first measured value from the second measured value ("RBC-O"-"RBC-I"). When the exponent value is a division value, the exponent value approaches to 1 as the degree of chronic kidney disease is milder. When the exponent value is a subtraction value, the exponent value approaches to 0 as the degree of chronic kidney disease is milder.

The calculated exponent value is compared with a reference range of each exponent value set for each stage of chronic kidney disease. The reference range can be preset. The reference range is not limited as long as it is within the range of the exponent value that can accurately classify the six stages of chronic kidney disease. For example, the exponent value is calculated for the peripheral blood of a group of chronic kidney disease patients of each stage that has already been staged and the peripheral blood of a healthy person group, and the range of the exponent value that can most accurately classify the patient group at each stage can be set as the reference range. As to "the range of the exponent value that can be most accurately classify", it is possible to obtain an exponent value indicating the boundary between the healthy person group and the patient group at each stage, and determine the exponent value indicating the boundary as the upper limit value or the lower limit value of the reference range of each stage. For example, the lower limit value of the reference range of the exponent value determined as the stage G1 can be set as an exponent value that can most accurately classify the healthy person group and the patient group of the stage G1. The upper limit value of the reference range of the exponent value determined as the stage G1 can be set as an exponent value that can most accurately classify the patient group of the stage G1 and the patient group of the stage G2. The reference ranges of other stages can also be set similarly. "The exponent value that can most accurately classify" can be appropriately set based on indices such as sensitivity, specificity, positive predictive value and negative predictive value, depending on the purpose of the examination. "The exponent value that can most accurately classify" can be also determined by a ROC curve (Receiver Operating Characteristic curve), a discriminant analysis method, a mode method, a Kittler method, a 3σ method, a p-tile method, and the like.

In the present embodiment, by comparing the exponent value calculated from the first measured value and the second measured value with each of the reference ranges, within which stage of the reference range the exponent value falls is determined. It is suggested that the subject collected from which the blood sample is collected is in a stage of chronic kidney disease linked to the reference range to which the exponent value corresponds. Suggesting the stage of chronic kidney disease includes determining that the subject is in a stage of chronic kidney disease linked to the reference range to which the exponent value corresponds.

[2-2. Determination Apparatus]

The determination apparatus 6 of the present embodiment determines the stage of chronic kidney disease, based on the number of red blood cells contained in a blood sample collected from a subject.

Figure 5:
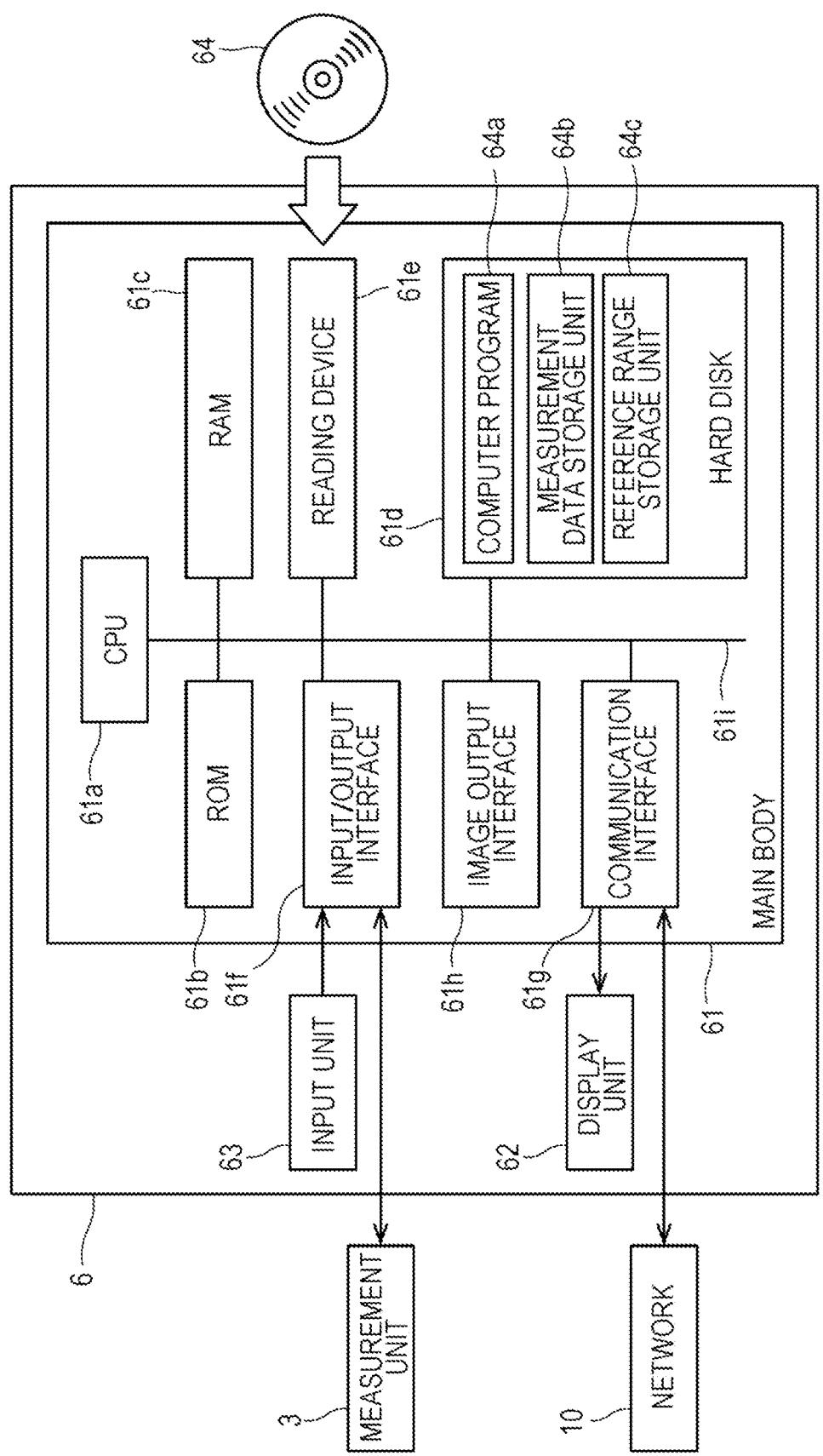
FIG. 5 is a configuration diagram of an apparatus for determining the stage of chronic kidney disease.

The determination apparatus 6 is configured by a computer. FIG. 5 is a block diagram showing the configuration of the determination apparatus 6. As shown in FIG. 5, a computer 6 includes a main body (control unit) 61, a display unit (output unit) 62, and an input unit 63. The main body 61 includes a CPU 61a, a ROM 61b, a RAM 61c, a hard disk 61d, a reading device 61e, an input/output interface 61f, a communication interface 61g and an image output interface 61h, and the CPU 61a, the ROM 61b, the RAM 61c, the hard disk 61d, the reading device 61e, the input/output interface 61f, the communication interface 61g and the image output interface 61h are connected via a bus 61i.

The CPU 61a can execute a computer program.

In the hard disk (storage device) 61d, various computer programs 64a to be executed by the CPU 61a, such as operating systems and application programs, and data used for executing the computer programs are installed. The hard disk (storage device) 61d also functions as a measurement data storage unit 64b and a reference range storage unit 64c.

The computer program 64a includes programs for controlling the measurement unit, analyzing the measurement data, outputting information, and the like. The computer program 64a can be recorded on a portable recording medium 64 such as a CD-ROM. The reading device 61e can read the computer program 64a recorded on the recording medium 64.

The computer program 64a is not only provided by the portable recording medium 64 but can also be provided from an external device communicably connected to the computer 6 by a network 10 (whether wired or wireless) through the network 10.

The image output interface 61h is connected to a display unit (output unit) 62 configured by a display or the like. Therefore, the determination apparatus 6 can display (output) various kinds of information.

The determination apparatus 6 may be integral with the information processing unit 5.

Figure 6:
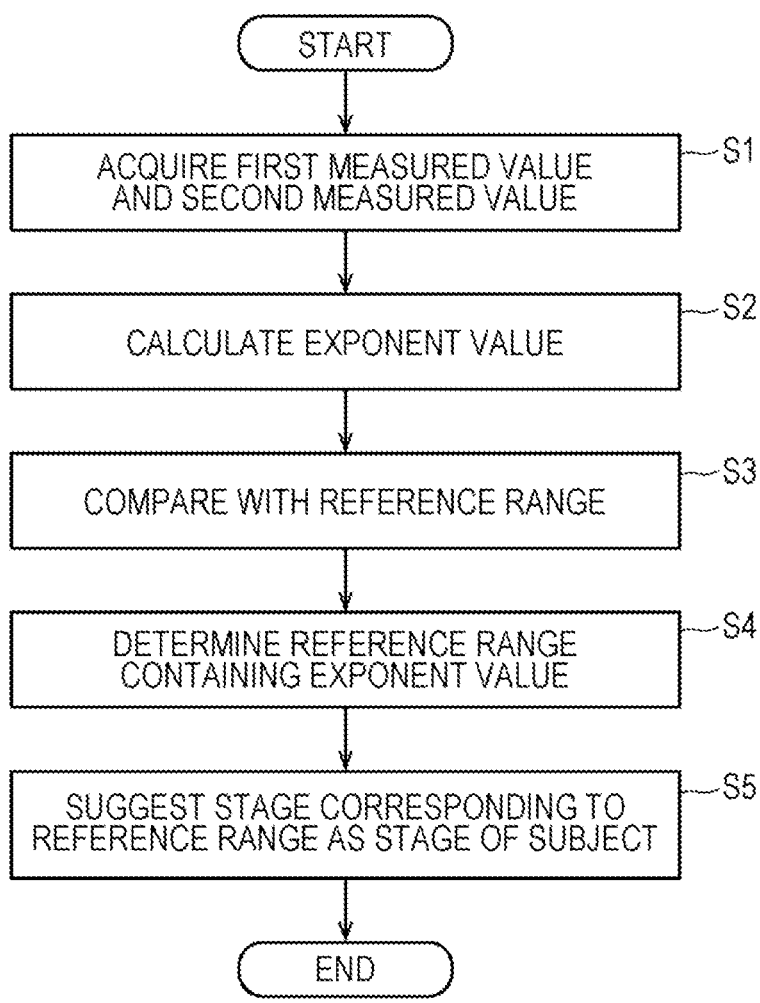
FIG. 6 is a flow chart showing operations of an apparatus for determining the stage of chronic kidney disease.

FIG. 6 shows the flow of operations of the determination apparatus 6. A control unit 61a of the determination apparatus 6 receives an input of processing start from the operator from the input unit 63. Upon receipt of this input, in step S1, the control unit 61a acquires a first measured value indicating red blood cell count measured by electrical resistance measurement method and a second measured value indicating red blood cell count measured by optical measurement method from the input/output unit 63, the measurement unit 3 or the network 10. The control unit 61a stores the measured values in the measurement data storage unit 64b. In step S2, the control unit 61a calculates an exponent value for the determination from the first measured value and the second measured value. In step S3, the control unit 61a compares the exponent value with each reference range determined for each stage of chronic kidney disease stored in the reference range storage unit 64c. In step S4, the control unit 61a determines a reference range containing the exponent value. In step S5, the control unit 61a suggests that the subject is in a stage corresponding to the reference range determined in the determination step.

Regarding terms such as "chronic kidney disease", "subject", "blood sample", "first measured value", "second measured value", "exponent value", "reference range", and "suggest", the description given in 2-1. above is incorporated herein.

Steps S1 to S5 above are controlled by a computer program. The computer program may be stored in a semiconductor memory element such as a hard disk or a flash memory, or a storage medium such as an optical disk. The storage format of the program in the storage medium is not limited as long as the presented device can read the program. Storage into the storage medium is preferably nonvolatile.

[3. Method and Apparatus for Determining Therapeutic Effect by Erythropoietic Factor Preparation]

[3-1. Determination Method]

One embodiment relates to a method for determining a therapeutic effect by an erythropoietic factor preparation. Determining the therapeutic effect includes assisting in determination of the therapeutic effect. The method determines a therapeutic effect of the erythropoietic factor preparation from an exponent value calculated with respect to red blood cell count in a blood sample collected from a subject before starting administration of an erythropoietic factor preparation and an exponent value calculated with respect to red blood cell count in a blood sample collected after starting administration of the preparation.

In the present embodiment, the erythropoietic factor preparation includes epoetin alfa, epoetin beta, darbepoetin alfa, epoetin beta pegol, and the like.

In this embodiment, the subject is a patient suffering from anemia, and preferably a patient suffering from renal anemia. The renal function of the subject may be normal, but it is preferably a patient who has suffered renal dysfunction or chronic kidney disease. The sex and age of the subject are not limited.

For the "blood sample", the description given in 2-1. above is incorporated herein by reference.

In the present embodiment, a first time point is not limited as long as it is before a second time point. The interval between the first time point and the second time point is about 5 days, 10 days, 30 days, 45 days, 60 days, or 90 days. Preferably, the first time point is before starting administration of an erythropoietic factor preparation. "Before starting administration of an erythropoietic factor preparation" refers to before the first administration of an erythropoietic factor preparation when the subject has no experience of receiving administration of the erythropoietic factor preparation. Even when the subject has an experience of receiving administration of the erythropoietic factor preparation, the lifespan of red blood cells is about 120 days. Therefore, when 120 days have passed since the end of the previous administration of the erythropoietic factor preparation, the subject may be regarded as a person who has no experience of receiving administration of the erythropoietic factor preparation. The second time point is after starting administration of the erythropoietic factor preparation.

In the present embodiment, for a blood sample collected from a subject at the first time point, a first exponent value is initially calculated from a first measured value indicating red blood cell count measured by electrical resistance measurement method and a second measured value indicating red blood cell count measured by optical measurement method. Prior to the calculation of exponent value, for the blood sample collected from a subject at the first time point, a first measured value indicating red blood cell count measured by the electrical resistance measurement method (RBC-I) and a second measured value indicating red blood cell count measured by the optical measurement method (RBC-O) may be acquired.

Prior to the calculation of exponent value, for the blood sample collected from a subject at the second time point, a third measured value indicating red blood cell count measured by the electrical resistance measurement method (RBC-I) and a fourth measured value indicating red blood cell count measured by the optical measurement method (RBC-O) may be acquired.

As the four measured values, the measured values measured by the measurement unit 3 may be acquired directly from the measurement unit 3 or may be acquired via a network (whether wired or wireless). The acquisition includes measuring. The acquisition may be performed by a human or may be performed by a control unit of an apparatus to be described later.

The first exponent value for determining the therapeutic effect is calculated from the first measured value and the second measured value. The exponent value includes a value obtained by dividing the first measured value by the second measured value ("RBC-I"/"RBC-O"), a value obtained by subtracting the second measured value from the first measured value ("RBC-I"-"RBC-O"), a value obtained by dividing the second measured value by the first measured value ("RBC-O"/"RBC-I"), or a value obtained by subtracting the first measured value from the second measured value ("RBC-O"-"RBC-I").

The second exponent value for determining the therapeutic effect is calculated from the third measured value and the fourth measured value. The exponent value includes, corresponding to the first exponent value, a value obtained by dividing the third measured value by the fourth measured value ("RBC-I"/"RBC-O"), a value obtained by subtracting the fourth measured value from the third measured value ("RBC-I"-"RBC-O"), a value obtained by dividing the fourth measured value by the third measured value ("RBC-O"/"RBC-I"), or a value obtained by subtracting the third measured value from the fourth measured value ("RBC-O"-"RBC-I").

In the present embodiment, the first exponent value is compared with the second exponent value calculated by the same calculation formula. When the second exponent value is improved over the first exponent value, it is suggested that the erythropoietic factor preparation works well in the subject.

When the first exponent value and the second exponent value are division values, the calculated second exponent value approaches to 1 as the erythropoietic factor preparation is more effective. Therefore, when the second exponent value is closer to 1 than the first exponent value, it is possible to determine that the second exponent value is improved over the first exponential value.

When the first exponent value and the second exponent value are subtraction values, the calculated second exponent value approaches to 0 as the erythropoietic factor preparation is more effective. Therefore, when the second exponent value is closer to 0 than the first exponent value, it is possible to determine that the second exponent value is improved over the first exponential value.

It is necessary to calculate the second exponent value by acquiring the third measured value and the fourth measured value each time a blood sample for determining the therapeutic effect is collected, in one subject. On the other hand, the first measured value and the second measured value for calculating the first exponent value may be acquired once for one subject.

Suggesting that the erythropoietic factor preparation is effective includes determining that the erythropoietic factor preparation is effective.

[3-2. Determination Apparatus]

The determination apparatus 7 of the present embodiment determines a therapeutic effect by an erythropoietic factor preparation, based on the number of red blood cells contained in a blood sample collected from a subject.

Figure 7:
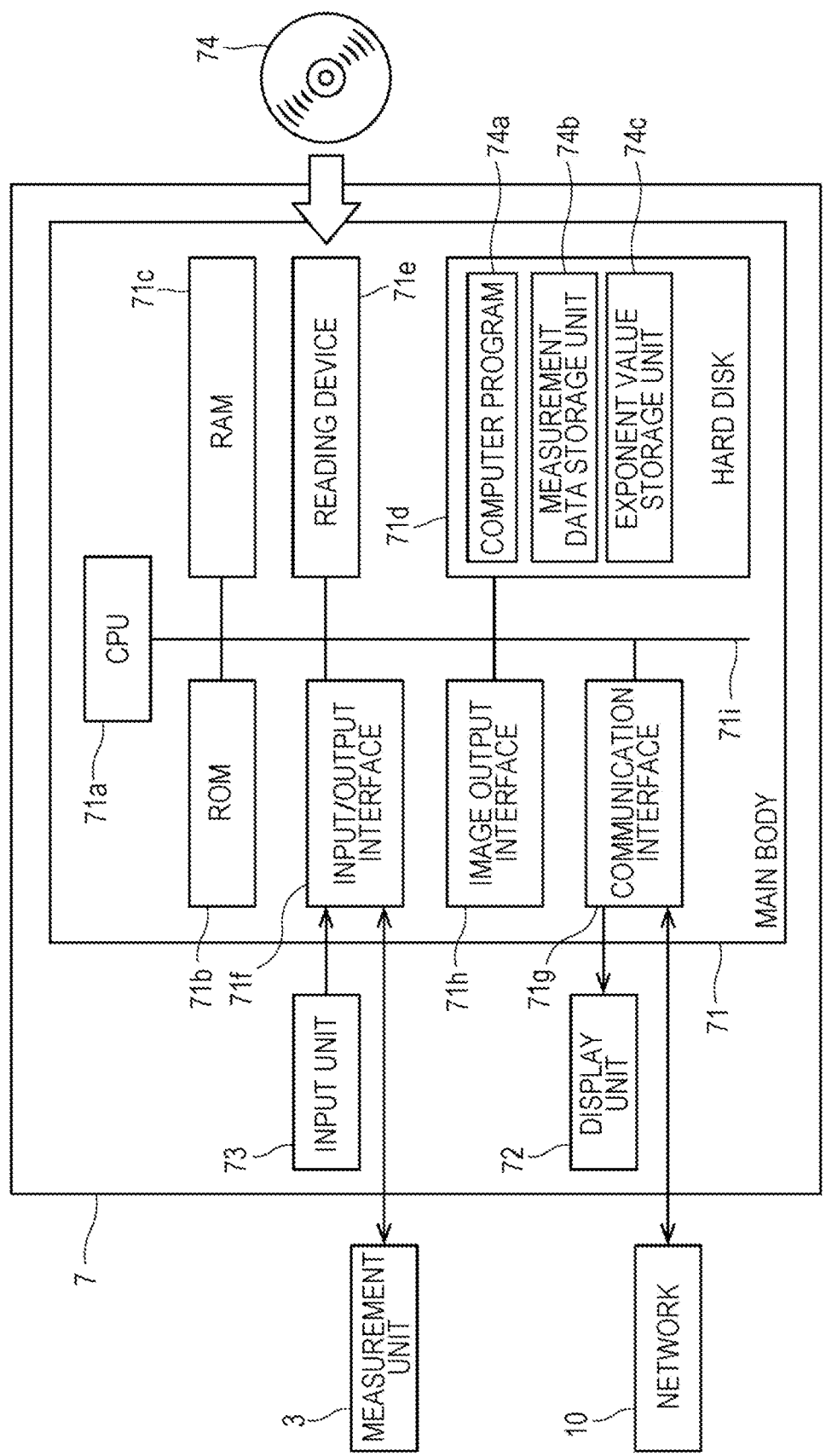
FIG. 7 is a configuration diagram of an apparatus for determining a therapeutic effect by an erythropoietic factor preparation.

The determination apparatus 7 is configured by a computer. FIG. 7 is a block diagram showing the configuration of the determination apparatus 7. As shown in FIG. 7, a computer 7 includes a main body (control unit) 71, a display unit (output unit) 72, and an input unit 73. The main body 71 includes a CPU 71a, a ROM 71b, a RAM 71c, a hard disk 71d, a reading device 71e, an input/output interface 71f, a communication interface 71g and an image output interface 71h, and the CPU 71a, the ROM 71b, the RAM 71c, the hard disk 71d, the reading device 71e, the input/output interface 71f, the communication interface 71g and the image output interface 71h are connected via a bus 71i.

The CPU 71a can execute a computer program.

In the hard disk (storage device) 71d, various computer programs 74a to be executed by the CPU 71a, such as operating systems and application programs, and data used for executing the computer programs are installed. The hard disk 71d also functions as a measurement data storage unit 74b and an exponent value storage unit 74c.

The computer program 74a includes programs for controlling the measurement unit, analyzing the measurement data, outputting information, and the like. The computer program 74a can be recorded on a portable recording medium 74 such as a CD-ROM. The reading device 71e can read the computer program 74a recorded on the recording medium 74.

The computer program 74a is not only provided by the portable recording medium 74 but can also be provided from an external device communicably connected to the computer 7 by a network 10 (whether wired or wireless) through the network 10.

The image output interface 71h is connected to a display unit (output unit) 72 configured by a display or the like. Therefore, the determination apparatus 7 can display (output) various kinds of information.

The determination apparatus 7 may be integral with the information processing unit 5.

Figure 8:
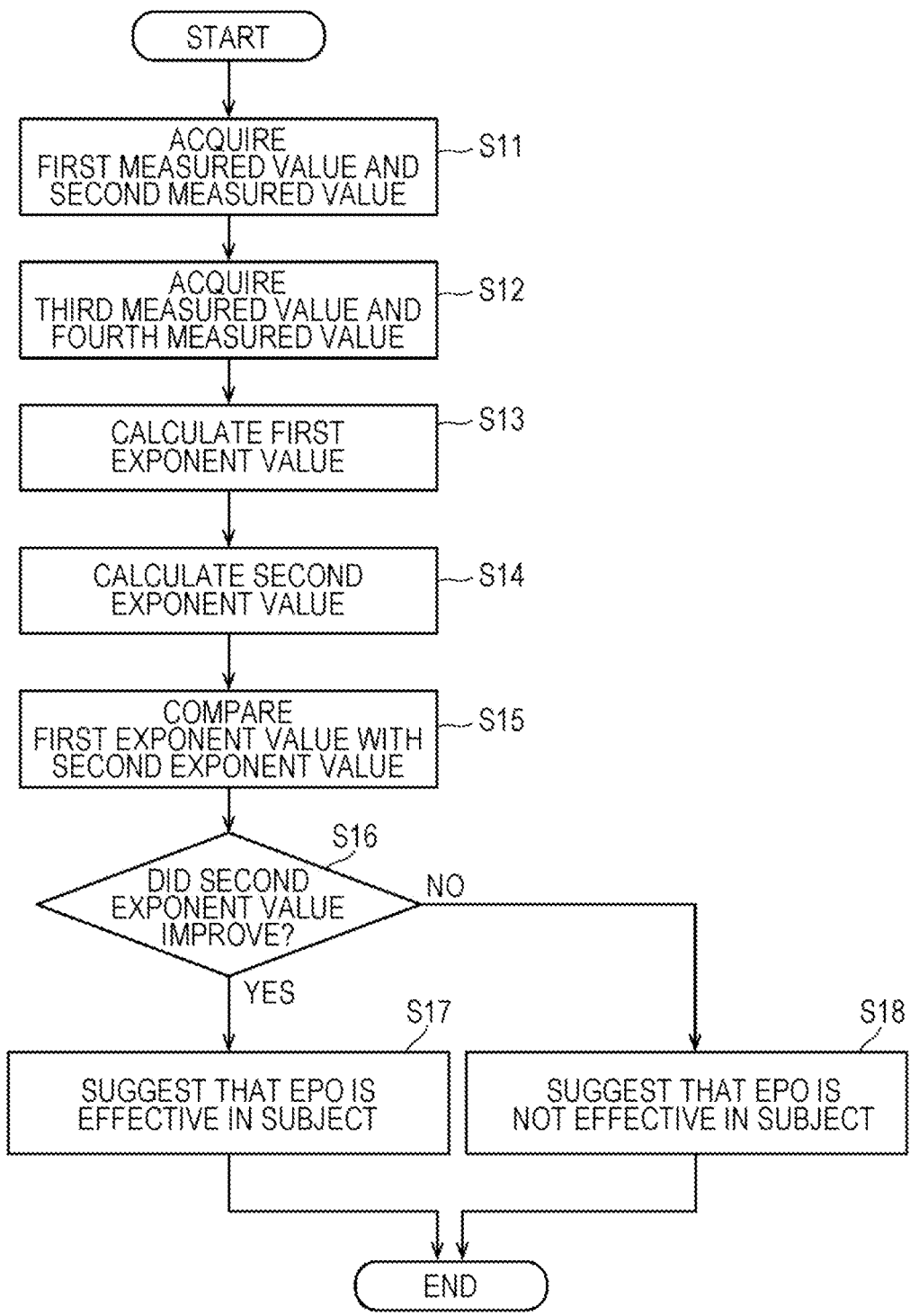
FIG. 8 is a flow chart showing operations of an apparatus for determining a therapeutic effect by an erythropoietic factor preparation.

FIG. 8 shows the flow of operations of the determination apparatus 7. A control unit 71a of the determination apparatus 7 receives an input of processing start from the operator from the input unit 73. Upon receipt of this input, in step S11, as to a blood sample collected from a subject before starting administration of an erythropoietic factor preparation, the control unit 71a acquires a first measured value indicating red blood cell count measured by electrical resistance measurement method and a second measured value indicating red blood cell count measured by optical measurement method from the input/output unit 73, the measurement unit 3 or the network 10. The control unit 71a stores the measured values in the measurement data storage unit 74b. In step S12, as to a blood sample collected from the same subject as the subject after starting administration of an erythropoietic factor preparation, the control unit 71a acquires a third measured value indicating red blood cell count measured by the electrical resistance measurement method and a fourth measured value indicating red blood cell count measured by the optical measurement method from the input/output unit 73, the measurement unit 3 or the network 10. The control unit 71a stores the measured values in the measurement data storage unit 74b.

In step S13, the control unit 71a calculates the first exponent value for the determination from the first measured value and the second measured value. In step S14, the control unit 71a calculates the second exponent value for the determination from the third measured value and the fourth measured value. The first measured value and the second measured value and/or the first exponent value may be stored in advance in the exponent value storage unit 74c.

In step S15, the control unit 71a compares the first exponent value with the second exponent value. In step S16, when the control unit 71a determines that the second exponent value is improved ("YES") over the first exponential value, the control unit 71a suggests in step S17 that an erythropoietic factor preparation (EPO) is effective in the subject. Alternatively, in step S16, when the control unit 71a determines that the second exponent value is not improved ("NO") than the first exponential value, the control unit 71a suggests in step S18 that an erythropoietic factor preparation (EPO) is not effective in the subject.

Regarding terms such as "erythropoietic factor preparation", "subject", "blood sample", "first measured value", "second measured value", "third measured value", "fourth measured value", "exponent value", "improvement", and "suggest", the description described given in 3-1. above is incorporated herein.

Steps S11 to S18 above are controlled by a computer program. The computer program may be stored in a semiconductor memory element such as a hard disk or a flash memory, or a storage medium such as an optical disk. The storage format of the program in the storage medium is not limited as long as the presented device can read the program. Storage into the storage medium is preferably nonvolatile.

[4. Method and Apparatus for Predicting Onset of Cerebral Infarction]

[4-1. Prediction Method]

One embodiment relates to a method for predicting the onset of cerebral infarction. Predicting the onset of cerebral infarction includes assisting prediction of onset of cerebral infarction. The onset of cerebral infarction is predicted based on the number of red blood cells contained in a blood sample collected from a subject.

Cerebral infarction is an ischemic disease of the brain that develops due to embolism or thrombus. In the present embodiment, the onset of cerebral infarction is predicted in the subject before it develops.

The subject is not limited, but is preferably a human. The subject may be an individual having a risk factor of cerebral infarction (for example, hypertension, diabetes, dyslipidemia, heart disease, stress, smoking, mass drinking, dehydration, obesity, etc.), or may be an individual who does not have the risk factor. The subject may be an individual who undergoes antithrombotic therapy, diabetes treatment, hyperlipidemia treatment, cardiac disease treatment or the like, or may be an individual who has not undergone it.

For the "blood sample", the description given in 2-1. above is incorporated herein by reference.

In the present embodiment, an exponent value for the prediction is initially calculated from a first measured value indicating red blood cell count measured by electrical resistance measurement method and a second measured value indicating red blood cell count measured by optical measurement method. Prior to the calculation of exponent value, for the blood sample collected from a subject, a first measured value indicating red blood cell count measured by the electrical resistance measurement method (RBC-I) and a second measured value indicating red blood cell count measured by the optical measurement method (RBC-O) may be acquired. As the two measured values, the measured values measured by the measurement unit 3 may be acquired directly from the measurement unit 3 or may be acquired via a network (whether wired or wireless). The acquisition includes measuring. The acquisition may be performed by a human or may be performed by a control unit of an apparatus to be described later.

From the first measured value and the second measured value, an exponent value for predicting the onset of cerebral infarction is calculated from the two measured values. The exponent value includes a value obtained by dividing the first measured value by the second measured value ("RBC-I"/"RBC-O"), a value obtained by subtracting the second measured value from the first measured value ("RBC-I"-"RBC-O"), a value obtained by dividing the second measured value by the first measured value ("RBC-O"/"RBC-I"), or a value obtained by subtracting the first measured value from the second measured value ("RBC-O"-"RBC-I"). When the exponent value is a division value, the exponent value approaches to 1 as the possibility of the onset of cerebral infarction is lower. When the exponent value is a subtraction value, the exponent value approaches to 0 as the possibility of the onset of cerebral infarction is lower. Based on this premise, the calculated exponent value is compared with the reference range corresponding to each calculation formula shown in FIG. 9, for example.

In the comparison, when it is determined that the exponent value is outside the reference range, it is suggested that the subject develops cerebral infarction. Suggesting the onset of cerebral infarction includes determining that the subject develops cerebral infarction or that the subject has the possibility of developing cerebral infarction.

[4-2. Prediction Apparatus]

The prediction apparatus 8 of the present embodiment predicts the onset of cerebral infarction, based on the number of red blood cells contained in a blood sample collected from a subject.

Figure 10:
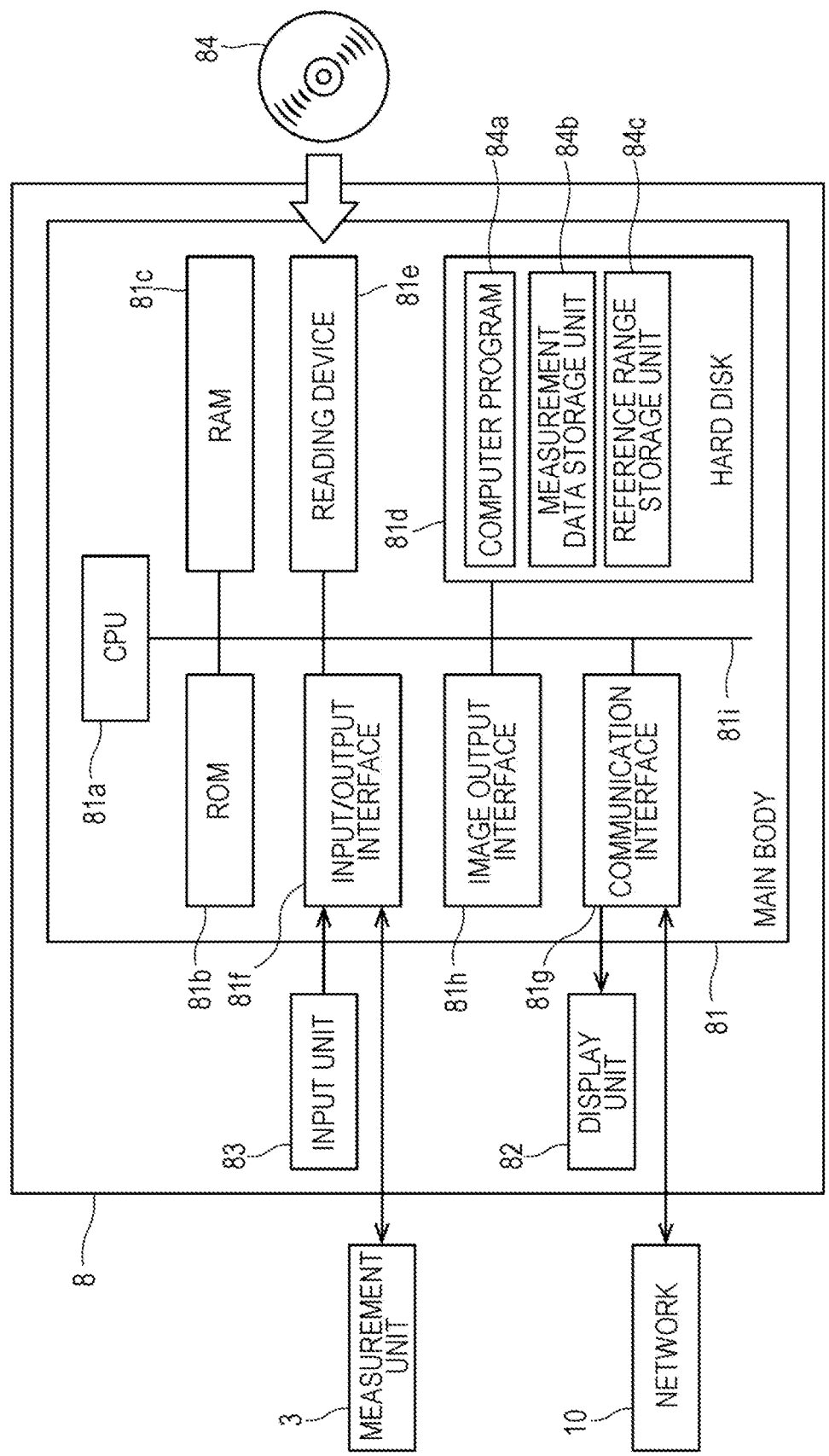
FIG. 10 is a configuration diagram of an apparatus for predicting the onset of cerebral infarction.

The prediction apparatus 8 is configured by a computer. FIG. 10 is a block diagram showing the configuration of the prediction apparatus 8. As shown in FIG. 10, a computer 8 includes a main body (control unit) 81, a display unit (output unit) 82, and an input unit 83. The main body 81 includes a CPU 81a, a ROM 81b, a RAM 81c, a hard disk 81d, a reading device 81e, an input/output interface 81f, a communication interface 81g and an image output interface 81h, and the CPU 81a the ROM 81b, the RAM 81c, the hard disk 81d, the reading device 81e, the input/output interface 81f, the communication interface 81g and the image output interface 81h are connected via a bus 81i.

The CPU 81a can execute a computer program.

In the hard disk (storage device) 81d, various computer programs 84a to be executed by the CPU 81a, such as operating systems and application programs, and data used for executing the computer programs are installed. The hard disk (storage device) 81d also functions as a measurement data storage unit 84b and a reference range storage unit 84c.

The computer program 84a includes programs for controlling the measurement unit, analyzing the measurement data, outputting information, and the like. The computer program 84a can be recorded on a portable recording medium 84 such as a CD-ROM. The reading device 81e can read the computer program 84a recorded on the recording medium 84.

The computer program 84a is not only provided by the portable recording medium 84 but can also be provided from an external device communicably connected to the computer 8 by a network 10 (whether wired or wireless) through the network 10.

The image output interface 81h is connected to a display unit (output unit) 82 configured by a display or the like. Therefore, the prediction apparatus 8 can display (output) various kinds of information.

The prediction apparatus 8 may be integral with the information processing unit 5.

Figure 11:
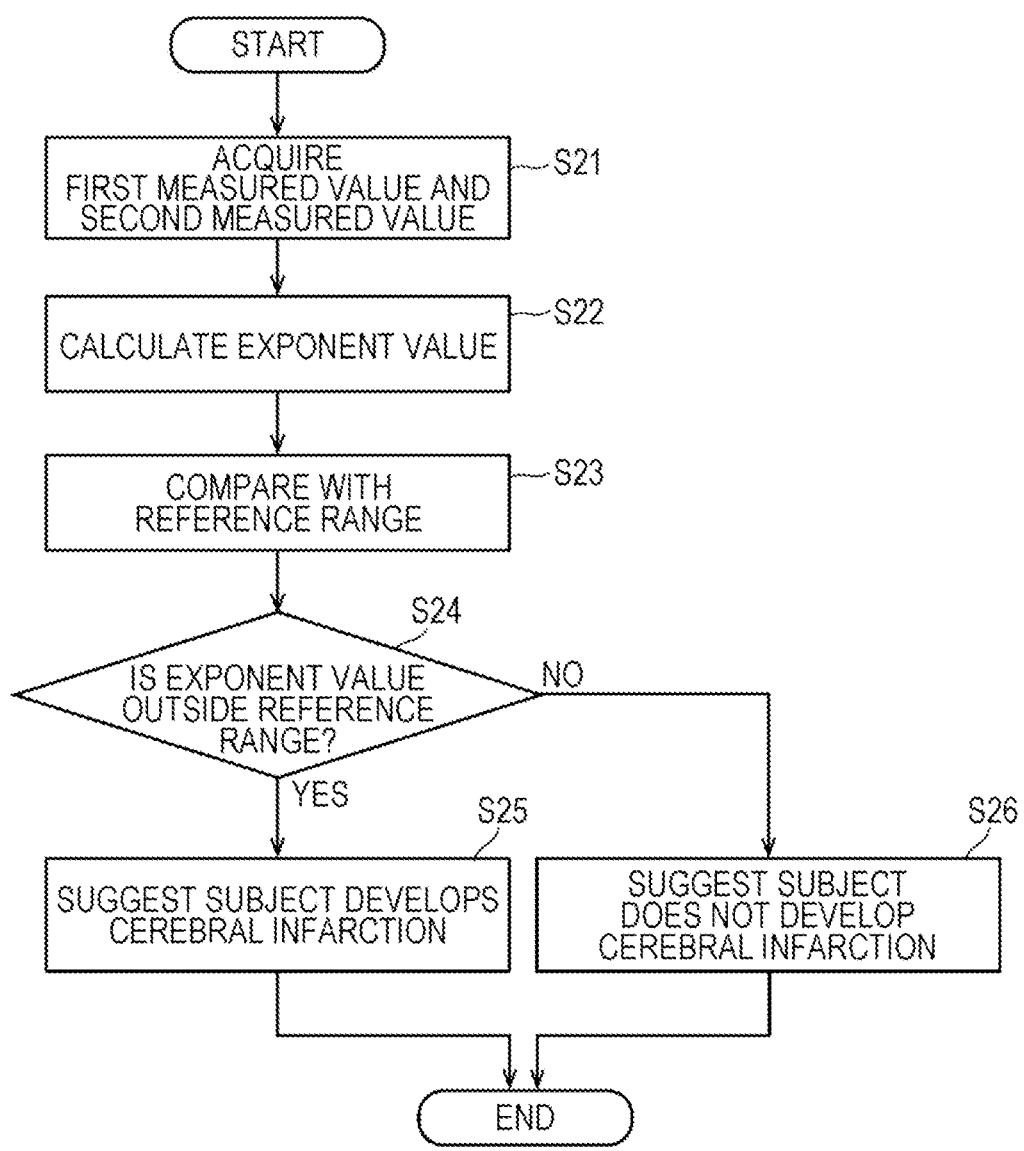
FIG. 11 is a flow chart showing operations of an apparatus for predicting the onset of cerebral infarction.

FIG. 11 shows the flow of operations of the prediction apparatus 8. A control unit 81a of the prediction apparatus 8 receives an input of processing start from the operator from the input unit 83. Upon receipt of this input, in step S21, the control unit 81a acquires a first measured value indicating red blood cell count measured by electrical resistance measurement method and a second measured value indicating red blood cell count measured by optical measurement method from the input/output unit 83, the measurement unit 3 or the network 10. The control unit 81a stores the measured values in the measurement data storage unit 84b. In step S22, the control unit 81a calculates an exponent value for the determination from the first measured value and the second measured value. In step S23, the control unit 81a compares the exponent value with the reference range stored in the reference range storage unit 84c. In step S24, when the control unit 81a determines that the exponent value is outside the reference range ("YES"), the control unit 81a suggests in step S25 that the subject develops cerebral infarction. In step S24, when the control unit 81a determines that the exponent value is not outside the reference range ("NO"), the control unit 81a suggests in step S26 that the subject does not develop cerebral infarction.

Regarding terms such as "cerebral infarction", "subject", "blood sample", "first measured value", "second measured value", "exponent value", "reference range", and "suggest", the description given in 2-1, above is incorporated herein.

Steps S1 to S5 above are controlled by a computer program. The computer program may be stored in a semiconductor memory element such as a hard disk or a flash memory, or a storage medium such as an optical disk. The storage format of the program in the storage medium is not limited as long as the presented device can read the program. Storage into the storage medium is preferably nonvolatile.

EXAMPLES

Hereinafter, the present invention will be described in more detail by way of examples, but the present invention is not to be construed as being limited to the examples.

I. Creation of Research Database

Patients who underwent blood tests after August 2015 at Department of Clinical Laboratory, the University of Tokyo Hospital were targeted. Data on blood counts and research items were regularly exported from a main body of a multi-item automatic blood cell analyzer (XN-9000, Sysmex Corporation, hereinafter referred to as "XN"). In parallel, the examination history, medication history, disease name, hospitalization history and outpatient visit history were output in CSV format from the medical information system of the University of Tokyo Hospital. These data were imported to a data warehouse installed in the Department of Clinical Laboratory, and the XN data and the clinical information were integrated and then unlinkably anonymized to create a consolidated database for research. In this research, analysis was performed using the consolidated database for the purpose of capturing the tendency of clinical laboratory values of patients with chronic kidney disease (CKD) and cerebral infarction. SQL Server (Microsoft) was used for database, and R was used for statistical analysis. This example was prepared upon approval by the Research Ethics Committee, Graduate School of Medicine and Faculty of Medicine, the University of Tokyo. In 22 months, it was possible to create a research database targeting 75 thousand people.

II. Example 1: Determination of the Stage of Chronic Kidney Disease

Figure 12A:
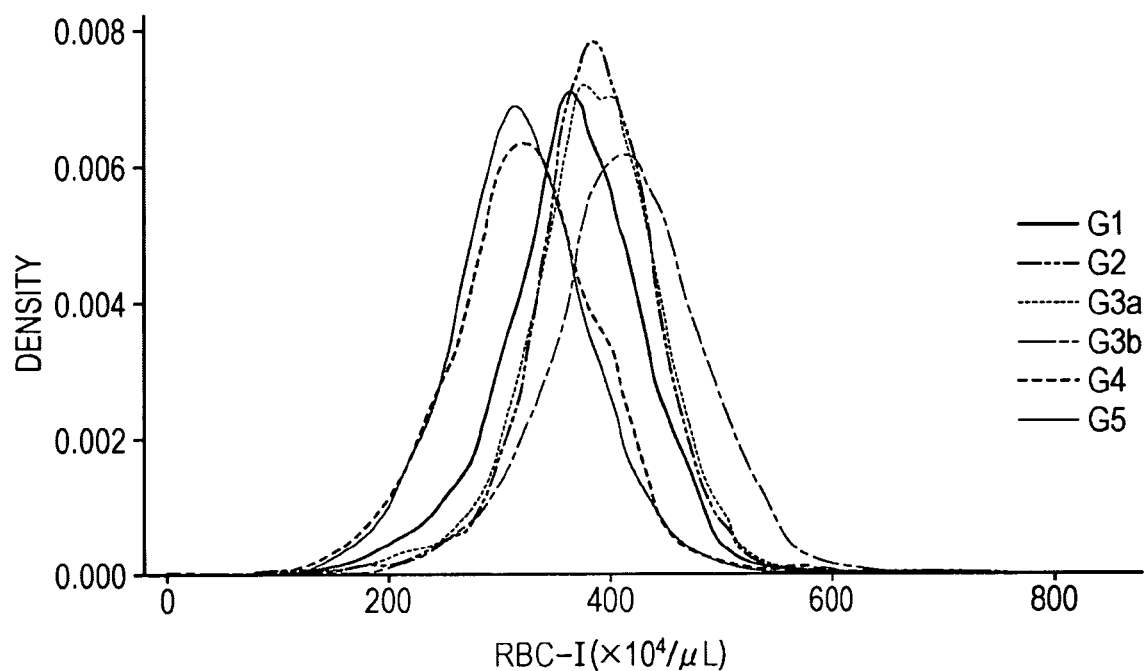
FIG. 12A shows a distribution of RBC-I in patient groups at each stage of CKD.
Figure 12B:
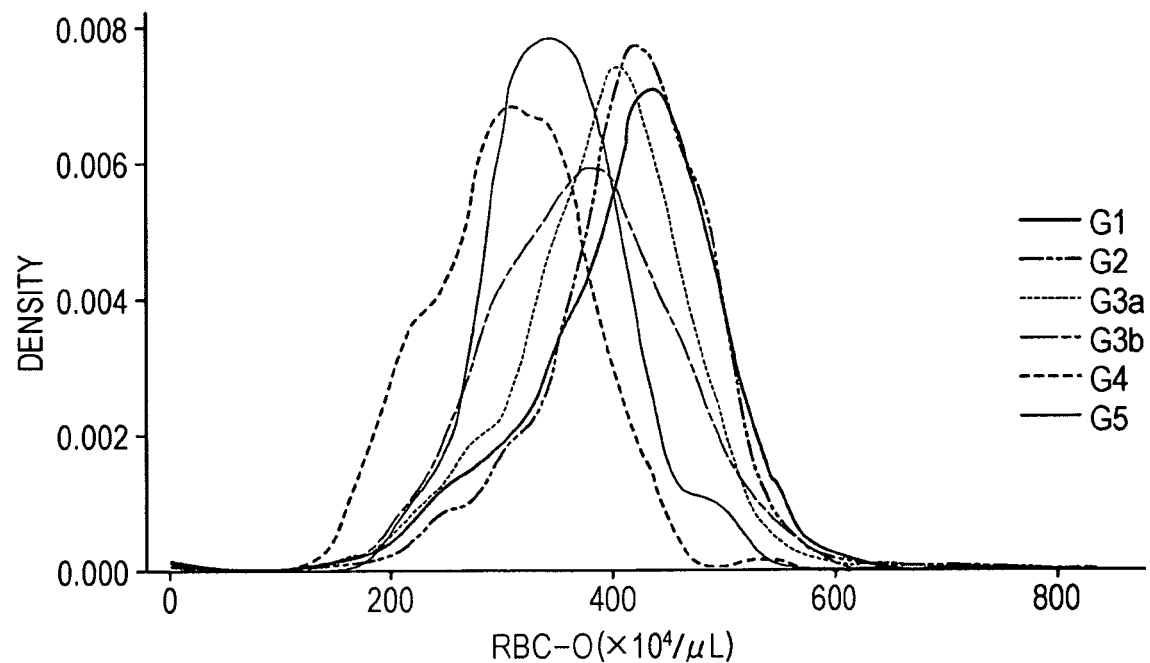
FIG. 12B shows a distribution of RBC-O in patient groups at each stage of CKD.

Data of CKD patients were extracted from the database created in I. above, and XN measurement data in the CKD patients in each stage were compared. As a result, red blood cell count in the CKD patients tended to be different depending on the measurement method. FIG. 12A shows the distribution of RBC-I in patient groups at each stage of CKD, and FIG. 12B shows the distribution of RBC-O in patient groups at each stage of CKD. The breakdown of the number of CKD patients in each stage is 3868 G1 patients, 16041 G2 patients, 5379 G3a patients, 1535 G3b patients, 329 G4 patients, and 310 G5 patients. In comparison between RBC-I and RBC-O, RBC-O became low value as the stage of CKD progressed. This results suggested that the stage of CKD can be determined by obtaining exponents of RBC-I and RBC-O.

Since RBC-O uses a surfactant at the time of measurement and micropores are formed in the erythrocyte membrane, the possibility that the difference in measurement method is affected was considered. It has been reported that CKD patients have shortened erythrocyte lifespan due to various factors, and the possibility that the RBC-O low value in the CKD patients reflects vulnerability of erythrocyte membranes is considered.

Figure 13:
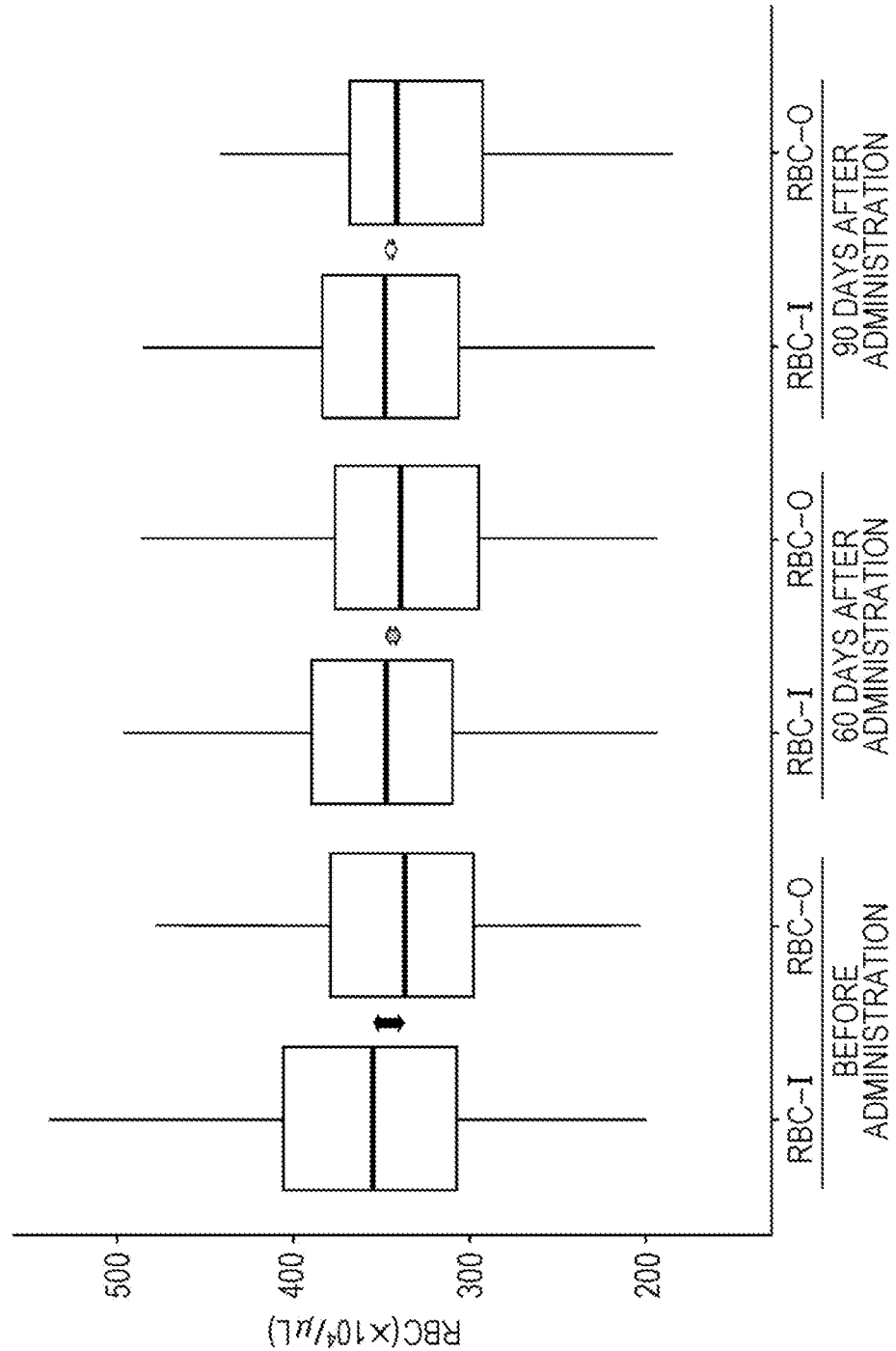
FIG. 13 shows box plots of RBC-I and RBC-O of a patient group before administration of an erythropoietic factor preparation, a patient group 60 days after administration, and a patient group 90 days after administration.

III. Example 2: Determination of the Effect of Erythropoietic Factor Preparation From the database created in I. above, data on renal anemia patients administered with an erythropoietic factor preparation were extracted, and RBC-I and RBC-O were compared among a patient group (182 patients) before administration of an erythropoietic factor preparation, a patient group (96 patients) at 60 days after administration, and a patient group (97 patients) after 90 days after administration. FIG. 13 shows box plots of each group.

As a result, before the erythropoietic factor preparation was administered, the average value of RBC-O was lower by about $30 \times 10^4/\mu l$ than the average value of RBC-I. The difference was improved 60 days after administration of the erythropoietic factor preparation, and the difference was further improved 90 days after administration of the erythropoietic factor preparation. This suggested that the therapeutic effect of the erythropoietic factor preparation can be determined by obtaining exponents of RBC-I and RBC-O.

IV. Example 3: Prediction of Onset of Cerebral Infarction

Figure 14A:
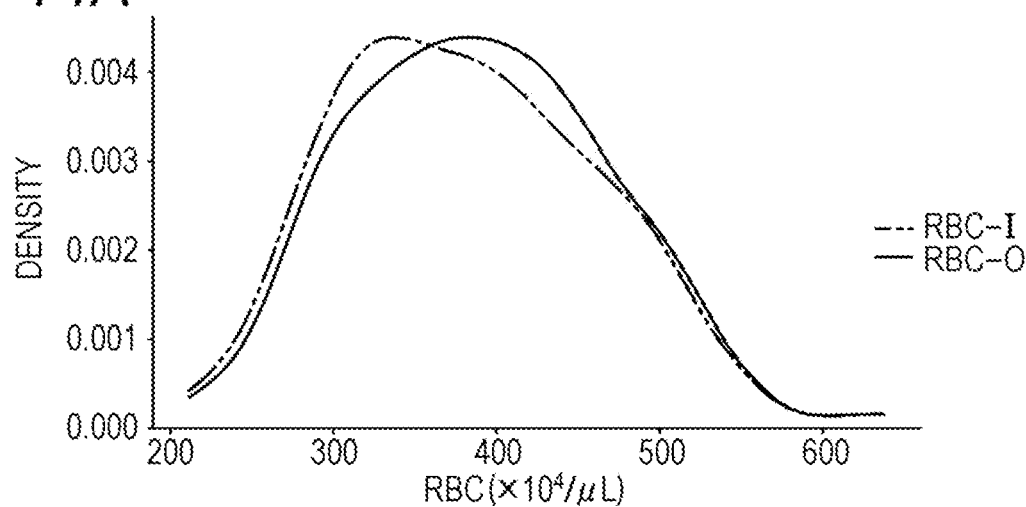
FIG. 14A shows RBC-I and RBC-O of a patient group who developed cerebral infarction within 2 weeks immediately after blood collection.
Figure 14B:
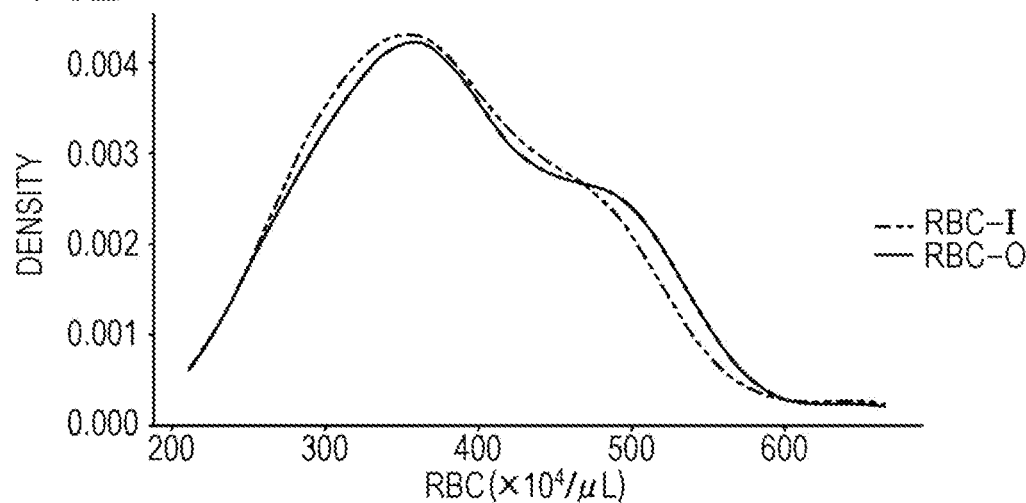
FIG. 14B shows RBC-I and RBC-O of the patient group immediately after to 1 week after the onset of cerebral infarction.
Figure 14C:
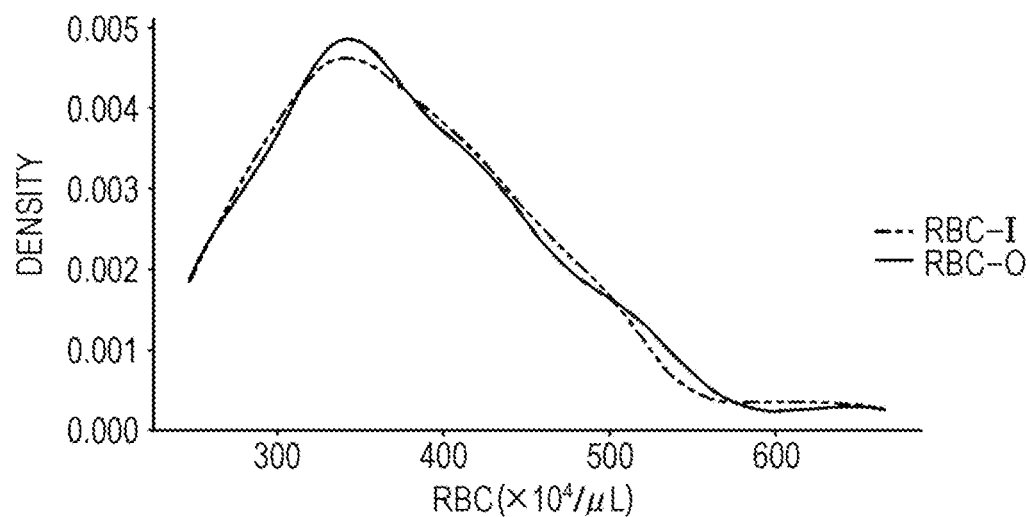
FIG. 14C shows RBC-I and RBC-O of the patient group 1 week after to 3 weeks after the onset of cerebral infarction.
Figure 15A:
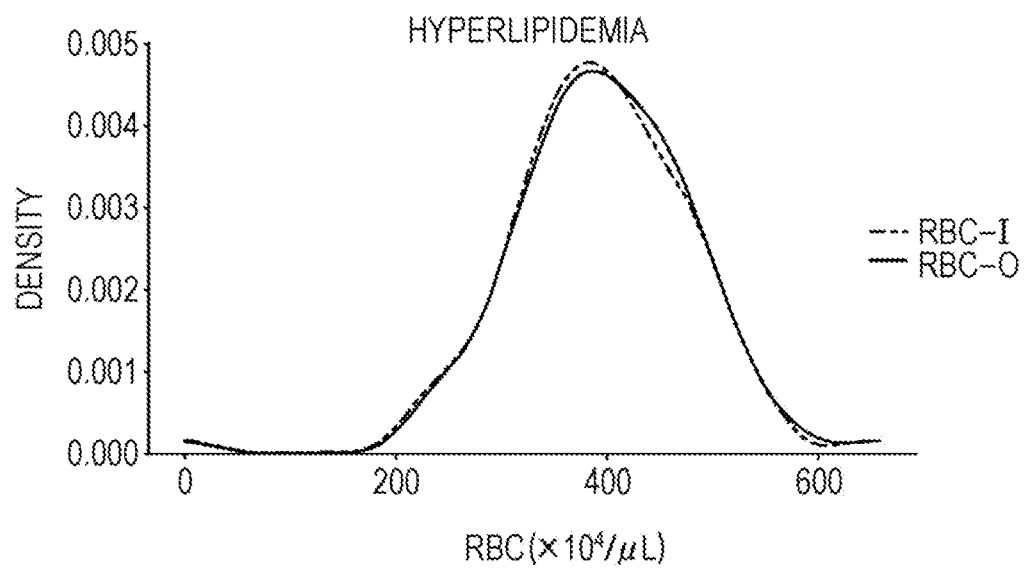
FIG. 15A shows RBC-I and RBC-O of a hyperlipidemia patient group.
Figure 15B:
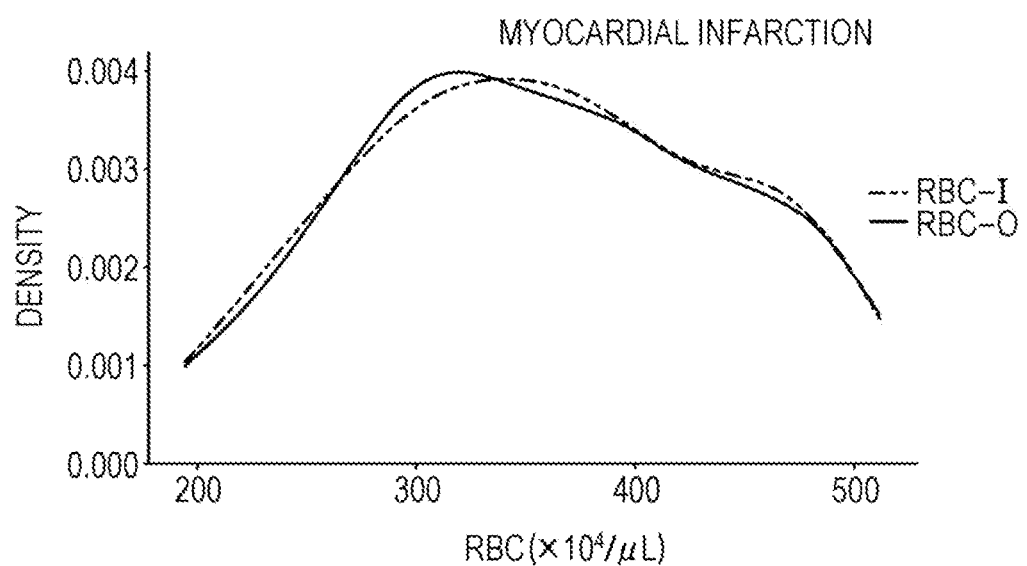
FIG. 15B shows RBC-I and RBC-O of a myocardial infarction patient group.

From the database created in I. above, data were extracted for a patient group (51 patients) who developed cerebral infarction within 2 weeks immediately after blood collection, a patient group (93 patients) immediately after to 1 week after the onset of cerebral infarction, a patient group (72 patients) 1 week after to 3 weeks after the onset of cerebral infarction, and RBC-I and RBC-O were compared. Data were also extracted for the myocardial infarction patient group (43 patients) and the hyperlipidemia patient group (97 patients) as control groups, and RBC-I and RBC-O were compared. FIG. 14A shows RBC-I and RBC-O of the patient group who developed cerebral infarction within 2 weeks immediately after blood collection, FIG. 14B shows RBC-I and RBC-O of the patient group immediately after to 1 week after the onset of cerebral infarction, and FIG. 14C shows RBC-I and RBC-O of the patient group 1 week after to 3 weeks after the onset of cerebral infarction. FIG. 15A shows RBC-I and RBC-O of the hyperlipidemia patient group, and FIG. 15B shows RBC-I and RBC-O of the myocardial infarction patient group.

As a result, it was revealed that RBC-I shows lower value than RBC-O only in the patient group who developed cerebral infarction within 2 weeks immediately after blood collection. This suggested that the onset of cerebral infarction can be predicted by obtaining exponents of RBC-I and RBC-O.

What is claimed is:

1. A method for assisting determination of a therapeutic effect by an erythropoietic factor preparation, comprising the steps of:

in a blood sample collected from a subject at a first time point, measuring a red blood cell count without treating red blood cells with a surfactant before measurement, measuring the red blood cell count after treating red blood cells with a surfactant, calculating a first exponent value from a first measured value indicating red blood cell count measured by electrical resistance measurement method and a second measured value indicating red blood cell count measured by optical measurement method;

administering the erythropoietic factor preparation to the subject;

for a blood sample collected from a subject at a second time point after administration of the erythropoietic factor preparation and after the first time point, calculating a second exponent value from a third measured value indicating red blood cell count measured by electrical resistance measurement method and a fourth measured value indicating red blood cell count measured by optical measurement method, comparing the first exponent value with the second exponent value; and determining, by a determination apparatus, that the erythropoietic factor preparation works well in the subject when the second exponent value is determined to be improved over the first exponent value.

2. The method of claim 1, wherein the first time point is prior to administration of the erythropoietic factor preparation to the subject.

3. The method of claim 1, wherein the first exponent value is a value obtained by dividing the first measured value by the second measured value, the second exponent value is a value obtained by dividing the third measured value by the fourth measured value, and when the second exponent value is closer to 1 than the first exponent value, it is determined that the second exponent value is improved over the first exponential value.

4. The method of claim 1, wherein the first exponent value is a value obtained by subtracting the second measured value from the first measured value, the second exponent value is a value obtained by subtracting the fourth measured value from the third measured value, and the second exponent value is determined to be improved over the first exponent value when the second exponent value is closer to 0 than the first exponent value.

5. The method of claim 1, wherein the first exponent value is a value obtained by dividing the second measured value by the first measured value, the second exponent value is a value obtained by dividing the fourth measured value by the third measured value, and when the second exponent value is closer to 1 than the first exponent value, it is determined that the second exponent value is improved over the first exponential value.

6. The method of claim 1, wherein the first exponent value is a value obtained by subtracting the first measured value from the second measured value, the second exponent value is a value obtained by subtracting the third measured value from the fourth measured value, and the second exponent value is determined to be improved over the first exponent value when the second exponent value is closer to 0 than the first exponent value.

7. The method according to claim 1, wherein the first measured value indicates red blood cell count measured without treating red blood cells with a surfactant before measurement, and the second measured value indicates red blood cell count measured by treating red blood cells with a surfactant before measurement.

* * * * *

UNITED STATES PATENT AND TRADEMARK OFFICE
CERTIFICATE OF CORRECTION

PATENT NO. : 11,703,441 B2
APPLICATION NO. : 16/145824
DATED : July 18, 2023
INVENTOR(S) : Hiromi Kataoka et al.

Page 1 of 1

It is certified that error appears in the above-identified patent and that said Letters Patent is hereby corrected as shown below:

On the Title Page

Title (54), and in the Specification, Column 1, Lines 1-7, the Title:
Delete "METHOD FOR PREDICTING ONSET OF CEREBRAL INFARCTION, METHOD FOR DETERMINING THERAPEUTIC EFFECT OF ERYTHROPOIETIC FACTOR PREPARATION, AND METHOD FOR DETERMINING STAGE OF CHRONIC KIDNEY"
Insert --METHOD FOR PREDICTING ONSET OF CEREBRAL INFARCTION, METHOD FOR DETERMINING THERAPEUTIC EFFECT OF ERYTHROPOIETIC FACTOR PREPARATION, AND METHOD FOR DETERMINING STAGE OF CHRONIC KIDNEY DISEASE--

Left column, item (71), the Applicants' address:
Delete "KAWASAKI GAKUEN Educational Foundation, Kurashiki (JP); THE UNIVERSITY OF TOKYO, Tokyo, (JP); SYSMEX CORPORATION, Kobe (JP)"
Insert --KAWASAKI GAKUEN Educational Foundation, Kurashiki-shi (JP); THE UNIVERSITY OF TOKYO, Tokyo, (JP); SYSMEX CORPORATION, Kobe-shi (JP)--

Left column, item (72), the Inventors' addresses:
Delete "Hiromi Kataoka, Kurashiki (JP); Yutaka Yatomi, Tokyo (JP); Akiko Masuda, Tokyo (JP); Hironori Shimosaka, Toyko (JP); Hajimu Kawakami, Kobe (JP)"
Insert --Hiromi Kataoka, Kurashiki-shi (JP); Yutaka Yatomi, Tokyo (JP); Akiko Masuda, Tokyo (JP); Hironori Shimosaka, Tokyo (JP); Hajimu Kawakami, Kobe-shi (JP)--

Left column, item (73), the Assignees' addresses:
Delete "KAWASAKI GAKUEN Educational Foundation, Kurashiki (JP); THE UNIVERSITY OF TOKYO, Tokyo, (JP); SYSMEX CORPORATION, Kobe (JP)"
Insert --KAWASAKI GAKUEN Educational Foundation, Kurashiki-shi (JP); THE UNIVERSITY OF TOKYO, Tokyo, (JP); SYSMEX CORPORATION, Kobe-shi (JP)--

Signed and Sealed this
Twenty-sixth Day of September, 2023

Katherine Kelly Vidal
*Director of the United States Patent and Trademark Office*